United States Patent [19]
Bicer

[11] Patent Number: 5,814,099
[45] Date of Patent: Sep. 29, 1998

[54] CENTRAL OPENING CURVED BILEAFLET HEART VALVE PROSTHESIS

[76] Inventor: Demetrio Bicer, 19161 Jasper Hill Rd., Trabuco Canyon, Calif. 92679

[21] Appl. No.: 694,418

[22] Filed: Aug. 12, 1996

[51] Int. Cl.[6] .......................................... A61F 2/24
[52] U.S. Cl. .................. 623/2; 137/512; 137/527
[58] Field of Search .................. 623/1, 2, 12, 66, 623/900; 137/512, 521, 527

[56] References Cited

U.S. PATENT DOCUMENTS

| | | |
|---|---|---|
| 2,822,819 | 2/1958 | Geeraert . |
| 3,445,863 | 5/1969 | Wada . |
| 3,608,097 | 9/1971 | Bellhouse et al. . |
| 3,903,548 | 9/1975 | Nakib . |
| 4,078,268 | 3/1978 | Possis . |
| 4,114,202 | 9/1978 | Roy et al. . |
| 4,291,420 | 9/1981 | Reul . |
| 4,339,831 | 7/1982 | Johnson . |
| 4,345,340 | 8/1982 | Rosen . |
| 4,406,022 | 9/1983 | Roy . |
| 4,416,029 | 11/1983 | Kaster . |
| 4,446,577 | 5/1984 | Meyer et al. . |
| 4,451,937 | 6/1984 | Klawitter ................................. 623/2 |
| 4,473,423 | 9/1984 | Kolff . |
| 4,488,318 | 12/1984 | Kaster . |
| 4,510,628 | 4/1985 | Kolff . |
| 4,822,999 | 4/1989 | Philippe et al. . |
| 4,863,459 | 9/1989 | Olin . |
| 5,026,391 | 6/1991 | McQueen et al. . |
| 5,078,739 | 1/1992 | Martin ........................................ 623/2 |
| 5,080,669 | 1/1992 | Tascon et al. . |
| 5,108,425 | 4/1992 | Hwang . |
| 5,116,367 | 5/1992 | Hwang et al. . |
| 5,123,920 | 6/1992 | Bokros . |
| 5,147,390 | 9/1992 | Campbell . |
| 5,152,785 | 10/1992 | Bokros et al. . |
| 5,192,309 | 3/1993 | Stupka et al. . |
| 5,236,449 | 8/1993 | Bokros et al. . |
| 5,314,467 | 5/1994 | Shu . |
| 5,326,372 | 7/1994 | Mhatre et al. ............................. 623/2 |
| 5,350,421 | 9/1994 | Stupka et al. ............................. 623/2 |
| 5,354,330 | 10/1994 | Hanson et al. . |
| 5,376,111 | 12/1994 | Bokros et al. . |
| 5,397,347 | 3/1995 | Cuilleron et al. . |
| 5,405,381 | 4/1995 | Olin ........................................... 623/2 |
| 5,405,382 | 4/1995 | Kukolinikov et al. . |
| 5,443,501 | 8/1995 | Barmada ................................... 623/2 |
| 5,628,791 | 5/1997 | Bokros et al. ............................. 623/2 |

OTHER PUBLICATIONS

Bicer–valve® Cardiac Prostheses Brochure, Canada Undated.
The Edwards–Duromedics™ Bileaflet valve Brochure, Irvine, CA Undated.
SJM Updated Brochure, Minnesota Apr. 1984.

*Primary Examiner*—Mickey Yu
*Assistant Examiner*—Francis K. Cuddihy
*Attorney, Agent, or Firm*—Stefan J. Kirchanski; Graham & James LLP

[57] ABSTRACT

A bileaflet prosthetic valve has leaflet pivots symmetrically or centrically located, thereby providing a central opening about twice the size of the two lateral openings. The valve opens from the center outward to provide nonturbulent central flow. The laminar leaflets are curved in cross-section so that the downstream edges of the leaflets are closer to the centerline of the cylindrical support ring when the leaflets are in an opened configuration. This position disposes the leaflets to favor valve closure when reverse flow of blood occurs. As the leaflets move toward a closed position, upstream edges of the leaflets begin to close the lateral openings, but this movement is opposed by blood flowing through these openings thereby providing a force to decelerate the leaflets and cushion their final closing. When the valve is fully closed, a single point of contact between the upstream edge of each leaflet and the support ring leaves a small gap between the support ring and the rest of the upstream edge and prevents the downstream edges from touching each other when they close the central opening.

28 Claims, 9 Drawing Sheets

CENTRAL OPENING CURVED BILEAFLET HEART VALVE PROSTHESIS

BACKGROUND OF THE INVENTION

1. Field of the Invention

The present invention relates to mechanical heart valve prostheses and, in particular, to improved heart valves having valve leaflets or occluders with curved as opposed to a straight cross-section which pivot on a centrally (centric) located axis of the leaflet, as opposed to eccentric (off-center), axes in moving between an open and a closed position.

2. Description of Related Art

A large number of prosthetic valves have been developed for valve replacement in the human heart. The replacement valve is intended to duplicate, as closely as possible, the properties of natural heart valves. The key hemodynamic flow properties of natural valves appear to be the ability to produce nonturbulent central flow. That is, natural valves open from the center so that flow is first established down the center of the conducting vessel. Because the natural valve opens fully, it offers little or no resistance to the flowing fluid so that laminar flow is established with the velocity of the flowing blood showing a gradient from the center of the vessel where flow is most rapid to the sides of the vessel where flow is slowest. There are no "dead areas" where blood flow stagnates which is important because stagnant blood may coagulate producing life threatening clots. Further, there are no areas of turbulent flow which can damage the red blood cells and the platelets, leading either to inappropriate blood clotting or to hemoglobin release and a host of other related problems.

Although it might seem logical to attempt to make a mechanical copy of the trileaflet form of a natural heart valve, various shortcomings of most mechanical valves have, thus far, made this impossible. Some of the first mechanical valves were of a ball-in-cage design, which were followed shortly by single leaflet (single occluder) valves. It was soon discovered that these devices failed to duplicate the hemodynamic properties of natural heart valves, resulting in replacement of theses devices by artificial valves with two leaflets (occluders). The early ball-in-cage valves and single leaflet (occluder) valves were superseded largely because they resulted in turbulent and/or noncentral blood flow. Unfortunately, many modern bileaflet valves still suffer from regions of stagnant blood flow and, because of the resulting risk of clots, most patients must be closely monitored and take anticoagulation drugs for life. These valves also cause turbulent noncentral flow, which contributes to hemolysis (hemoglobin leakage from damaged red blood cells), inappropriate clotting, and blood vessel damage. Furthermore, some modern low profile bileaflet designs suffer from the very real problem of entrapment of an occluder by cardiac structures because a significant portion of the occluder projects downstream beyond the valve when the valve is in the opened position.

Figure 1A:
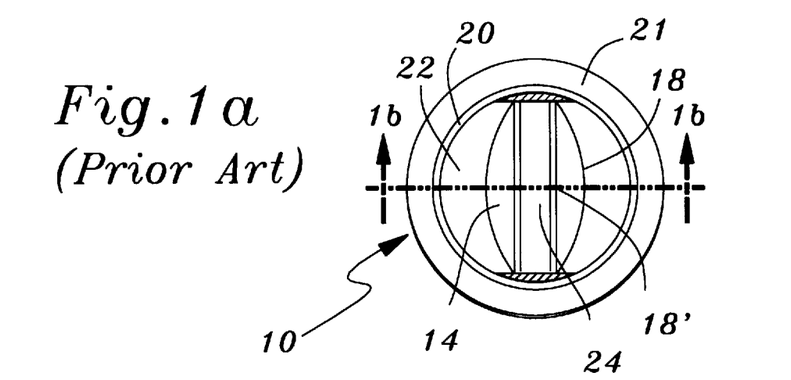
FIG. 1a shows a plan view of the upstream side of an open prior art bileaflet valve having eccentrically placed pivots and planar leaflets.

As an aid to understanding the present invention, a typical prior art bileaflet valve is illustrated and explained. A typical prior art bileaflet valve 10 (FIG. 1a) comprises a cylindrical support ring 20 to which two leaflets 14 are pivotally attached as shown in FIG. 1a, which illustrates an eccentric (off-center) valve 10 wherein the pivots 12 are placed very close to an upstream edge 18' of the leaflet 14. Most bileaflet heart valves are eccentrically pivoted because the off-center pivot placement promotes valve closing as will be explained below. Actually, there are at least three different leaflet designs in common use with a myriad of variations in the pivots 12. FIG. 1a shows a surface view of an open eccentric valve from the upstream side (closest to origin of forward flowing blood). The valve of FIG. 1a has laminar leaflets 14 that are flat in cross-section. FIG. 1a' shows a similar view of a similar valve except that the leaflets 14 are curved in cross-section in a plane perpendicular to the direction of blood flow through the valve (i.e., parallel to the plane of the page). FIG. 1a" shows another similar prior art valve wherein the leaflets 14 are curved in a plane parallel to the direction of blood flow.

Figure 1B:
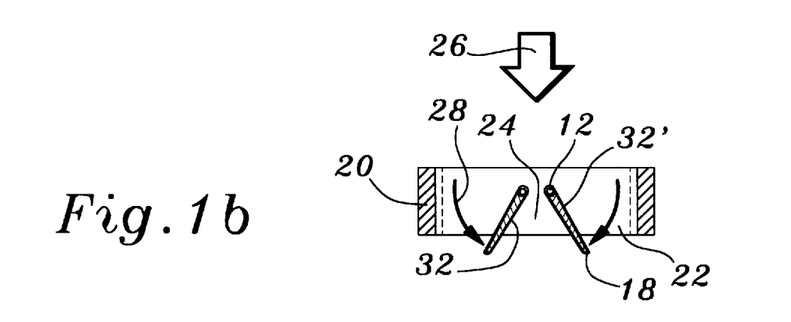
FIG. 1b shows a cross-sectional diagram of the prior art valve of FIG. 1a being opened by a forward flow of blood.
Figure 1C:
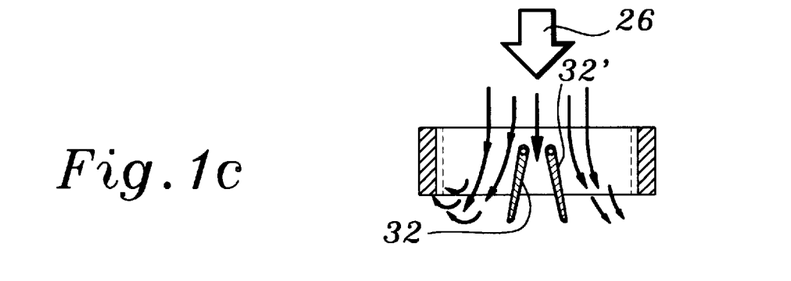
FIG. 1c shows the valve of FIG. 1a in an opened configuration showing turbulent blood flow.

When blood flow (arrow 26) is in the opening direction, the blood strikes an upstream surface 32' of the leaflet 14 which pivot along arrows 28 (FIGS. 1b, 1b', 1b") and the valve opens. This type of valve is side opening (side passages open first) and may be identified as such because the left-hand leaflet (viewed with a downstream edges 18 pointing down) pivots counterclockwise while the right-hand leaflet pivots clockwise. Conversely, in a center opening bileaflet valve (FIG. 2) the left-hand leaflet, viewed in the same orientation, pivots clockwise on opening. Note, also, that the off-center position of pivots 12 results in the valve 10 having lateral openings 22 that are larger than a central opening 24. The larger lateral passageways and the side opening property create nonideal blood flow conditions of nonlaminar flow (arrows in FIGS. 1c, 1c", 1c"). Further, in the fully open position, movement of the leaflets 14 is mechanically restricted so that the leaflets 14 form an angle with the blood flow 26 to assure proper closing of the valve (note FIGS. 1c, 1c'). This angle creates an adverse boundary layer separation in the blood flow and increases friction of the blood flow. Alternatively, the leaflets 14 may hang parallel to the blood flow in the open position, but with their downstream edges 18 curved slightly away from the centerline of the support ring 20 to favor closing (FIG. 1c"). Again, this design tends to increase blood flow turbulence.

Figure 1D:
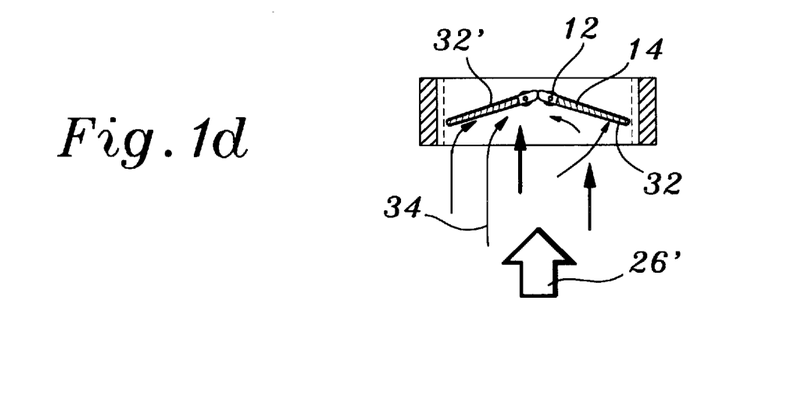
FIG. 1d shows the valve of FIG. 1a closing in response to reversed blood flow.

When blood flow 26' is reversed (FIGS. 1d, 1d', 1d"), the back-flowing blood (arrow 26') preferentially strikes downstream surfaces 32 of the leaflets 14 (this effect is amplified by curving the leaflet edges or by angling the leaflets in the opened position), causing them to pivot along arrows 28'. Because the leaflets 14 pivot off-center, most of the downstream surface 32 is on one side of the pivot 12. This favors closure of the valve because the opposing force generated by blood striking the downstream surface 32 of that part of the leaflet 14 on the other side of the pivot 12 is very small. As the valve 10 closes, the leaflets 14 form a concave shape and the back-flowing blood is forced towards the center of the valve (arrows 34), creating a central turbulence. The dilemma, then, is that an off-center pivot design that ensures rapid valve closure does so at the sacrifice of central flow and at the price of turbulence and maximized drag. Virtually all commercial bileaflet heart prostheses currently use an off-center pivot design to ensure rapid valve closure when the direction of blood flow reverses.

The number of United States patents issued on prosthetic heart valves is truly amazing. The following discussion of relatively recent patents, as well as the numerous patents cited therein, give some idea of the scope of the prior art. The majority of recent disclosures appear to be directed towards off-center (eccentrically) pivoted bileaflet valves that open from the side; that is, these valves have larger side passageways than central passageways and open with the left-hand leaflet pivoting counterclockwise. U.S. Pat. No. 4,863,459 to Olin discloses a bileaflet valve that has highly eccentric pivots, has lateral passageways that are much larger than the central passageways with side opening (left-hand leaflet pivots counterclockwise), and has a very significant protrusion of the leaflets on the downstream side when the valve is open.

Many recent eccentric pivot patents have specialized pivot structures that allow the pivot point to shift in relation to the support ring 20 so that the leaflets essentially "hang" parallel to the blood flow in the open position. Typical is U.S. Pat. No. 5,080,669 to Tascon et al., which shows eccentric, slightly curved (downstream edges curved away from valve center) leaflets with pronounced side opening. U.S. Pat. No. 5,108,425 to Hwang also discloses a side opening valve where the left-hand leaflet pivots counter-clockwise. U.S. Pat. No. 5,123,920 to Bokros shows a side-opening eccentric pivot valve having stops that interact with complimentary structures on the leaflets 14 providing sliding engagement to cushion the final opening in a manner similar to that of Hwang or to that shown in U.S. Pat. No. 5,152,785 to Bokros et al.

Other side opening (left-hand leaflet pivots counterclockwise) eccentric pivot designs are found in U.S. Pat. No. 5,192,309 to Stupka et al. (cylindrical leaflets with slotted pivots), U.S. Pat. No. 5,314,467 to Shu (partially cylindrical leaflets with downstream edges curved away from the centerline in the open position), U.S. Pat. No. 5,376,111 to Bokros et al. (cylindrical leaflets with curved slots that substantially offset the pivots), and U.S. Pat. No. 5,397,347 to Cuilleron et al. (highly eccentric pivoted cylindrical leaflets).

There have also been a few true center opening (left-hand leaflet pivots clockwise) designs. For example, U.S. Pat. No. 4,078,268 to Possis shows a center opening design where the central passageway is considerably larger than the lateral passageways. However, the pivot is eccentrically placed, and the opened valve has leaflets that are straight in cross-section and that strongly protrude on the downstream side of the valve. The device disclosed in U.S. Pat. No. 4,114,202 to Roy et al. is also center opening, but it operates by having the leaflets essentially hinged from the sides of the valve support ring 20 (highly eccentric with no lateral openings). In this design the hinge includes large stagnant areas that can promote clotting and blood cell damage. U.S. Pat. No. 5,075,739 to Martin discloses another side hinged, center opening design with major downstream protrusions in the opened position. U.S. Pat. No. 4,676,789 to Sorensen et al. provides an alternative arrangement for a center opening valve (left-hand leaflet rotates clockwise). The leaflets are conical, rather than planar, and, while eccentrically pivoted from the base of the conical sections, are difficult to compare with the essentially planar leaflets of the other prior art discussed thus far.

A possible alternative to the eccentric pivot design would be a symmetric, centrically pivoted, design where the pivot axis would bisect an axis of bilateral symmetry of the leaflet 14. A centrically pivoted design should minimize protrusion of the leaflets 14 from the opened valve. The major apparent drawback of a planar leaflet of symmetric valve is that it does not close reliably (if at all). When the direction of blood flow is reversed in such a valve, there will be little or no tendency for the leaflets to resume the closed position. If fully open leaflets are unrestrained and parallel to the direction of fluid flow, they will remain so regardless of flow direction. One prior art method of ensuring leaflet closure is to restrict the range of leaflet motion so that the leaflets remain angled (discussed above in relation to eccentric valves) towards the direction of blood flow even when the valve is fully open. This solution is generally not acceptable because the angled leaflets cause turbulence and restrict blood flow so that the effective orifice area (EOA) is substantially reduced.

OBJECTS AND SUMMARY OF THE INVENTION

It is an object of the present invention to provide a prosthetic heart valve that opens from the center to provide a large central opening;

It is a further object of the present invention to provide a prosthetic heart valve which avoids damaging blood cells during valve closing;

It is a still further object of the present invention to provide a prosthetic heart valve which promotes nonturbulent, laminar flow when in an opened configuration;

It is another object of the present invention to provide a prosthetic heart valve that is a nonprofile valve wherein the leaflets do not extend beyond the downstream side of the support ring, thereby preventing leaflet entrapment or disturbance of any cardiac structures;

It is a further object of the present invention to provide a prosthetic heart valve that has a large central opening that has an area about twice that of the lateral openings;

It is a still further object of the present invention to provide a prosthetic heart valve wherein the outflow (downstream) orifice area of the lateral opening is larger than that of the inflow (upstream) orifice of the same opening;

It is a further object of the present invention to provide a prosthetic heart valve that avoids areas of stagnant blood and constantly washes valve surfaces during valve operation;

It is another object of the present invention to provide a prosthetic heart valve that reduces load, stress and operational noise; and It is another object of the present invention to provide a prosthetic heart valve utilizing a damping system to limit impact upon valve closing.

These and other objects are met by a bileaflet valve with laminar curved leaflets in which pivots are centrically and symmetrically located on the leaflets thereby providing a central opening about twice the size of the two lateral openings. The valve opens from the center outward to provide nonturbulent central flow. The laminar leaflets are curved in cross-section so that the downstream edges of the leaflets are closer to the centerline of the cylindrical support ring when the leaflets are in an opened configuration. This placement disposes the leaflets to favor valve closure when reverse flow of blood occurs. As the leaflets move toward a closed position, upstream edges of the leaflets begin to close the lateral openings, but this movement is opposed by blood flowing through these openings, thereby providing a force to decelerate the leaflets and cushion their final closing. When the valve is fully closed, there is a single point of contact between the upstream edge of each leaflet and the support ring, thereby leaving a small gap between the support ring and the rest of the upstream edge and preventing the downstream edges from actually touching each other when they close the central opening. Further, when the valve is fully closed, the leaflets form a convex surface which allows the blood to flow smoothly over that surface, thereby preventing turbulence and washing the entire valve.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 1a' shows a plan view of the upstream side of an open prior art bileaflet valve having eccentrically placed pivots and leaflets that are curved in a cross-section taken parallel to the plane of the page;

FIG. 1a" shows a plan view of the upstream side of an open prior art bileaflet valve having eccentrically placed pivots and leaflets curved in cross-section taken in a plane normal to that of the page;

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide a bileaflet heart valve prosthesis that provides nonturbulent central blood flow and controlled opening and closing velocities of the leaflets.

Figures 2A, 2F:
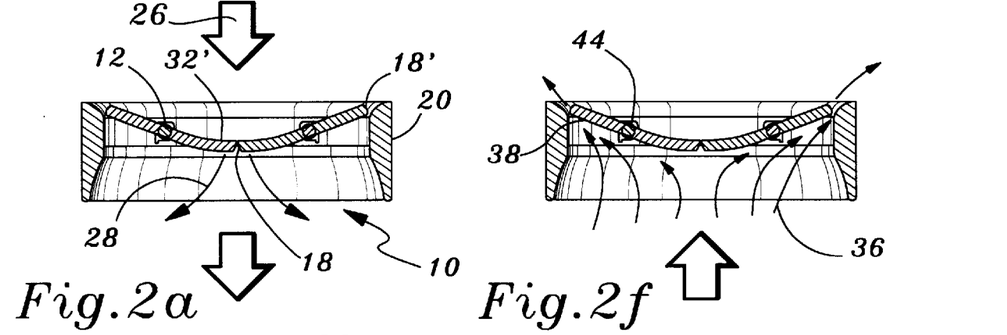
FIG. 2a shows a cross-sectional diagram of a symmetrically centrically pivoted bileaflet valve of the present invention in a closed configuration beginning to open.
FIG. 2f shows the valve of FIG. 2a fully closed configuration.

The present inventor has departed from the asymmetric eccentric designs prevalent in the prior art and has developed symmetric centric pivot designs that overcome the symmetric pivot shortcomings discussed above. A valve of the present invention, shown in the closed position in FIG. 2a, is a bileaflet design with pivots 12 placed along a symmetric, central axis. As explained above, a symmetric or centric valve has the pivots 12 placed so that the axis of pivoting bisects or nearly bisects an axis of bilateral symmetry of the leaflet 14 (i.e., the axis which divides the leaflet into two identical mirror images). When the closed valve is met by blood flow 26 in the front-flow direction, the blood presses against the upstream leaflet surfaces 32' (on the downstream half of the leaflet 14), causing the leaflets to pivot (arrows 28), causing a large central opening 24 to form as shown in FIG. 2d.

The symmetric or centric pivot valve opens from the center (left-hand leaflet pivoting clockwise) so that central flow is established first. The centric pivot placement ensures that the central opening 24 is about twice the size of the lateral openings 22, so that more blood flows through the center of the valve than through either of the lateral openings 22 (see FIG. 2c). When the valve is open, the laminar curved leaflets 14 freely align to be parallel to the blood flow direction. This ensures that the blood flow is laminar and nonturbulent. Furthermore, the flowing blood constantly sweeps both surfaces of the laminar leaflets 14, as well as the exposed recesses of the pivot points 12, thereby ensuring that there are no areas of stasis where blood clots may develop.

Figures 2B, 2E:
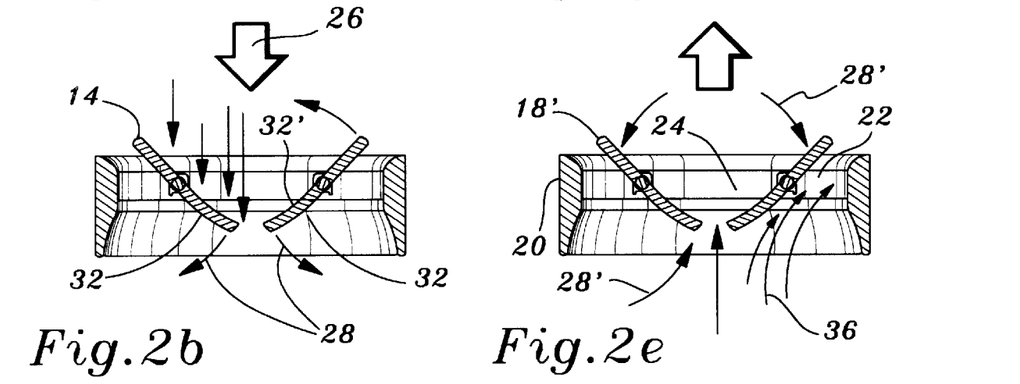
FIG. 2b shows the valve of FIG. 2a in an partially open configuration.
FIG. 2e shows the valve of FIG. 2a in an partially closed configuration.
Figure 2C:
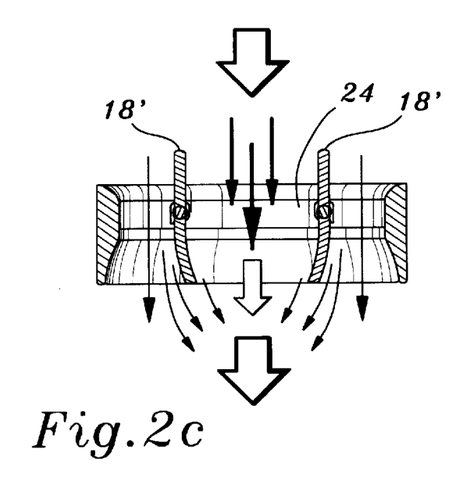
FIG. 2c shows the valve of FIG. 2a fully opened configuration.
Figure 2D:
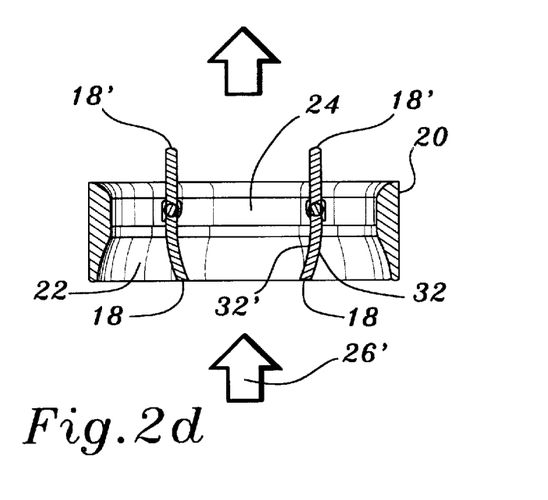
FIG. 2d shows a cross-sectional diagram of a symmetrically pivoted bileaflet valve of the present invention in an opened configuration beginning to close.
Figure 3A:
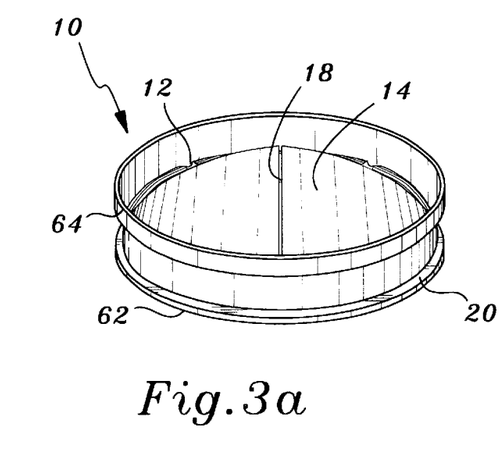
FIG. 3a shows a perspective view of the valve of FIG. 2 in the closed position.
Figure 3B:
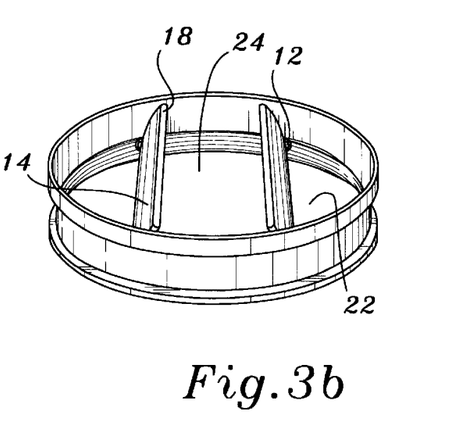
FIG. 3b shows a perspective view of the valve of FIG. 2 in the opened position.
Figure 4A:
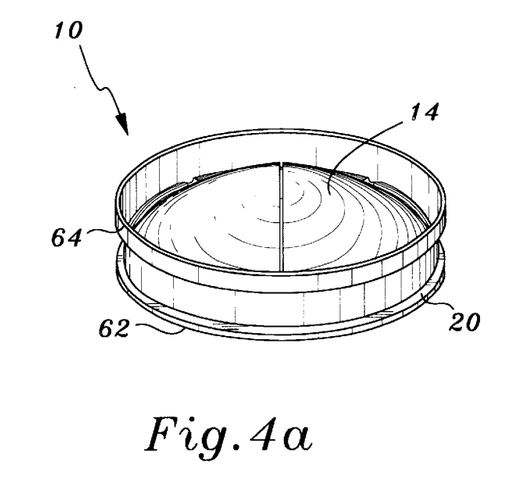
FIG. 4a shows a perspective view, in a closed position, of an alternative embodiment of the symmetric centrical pivot valve of the present invention wherein the leaflets have a spherical surface.
Figure 4B:
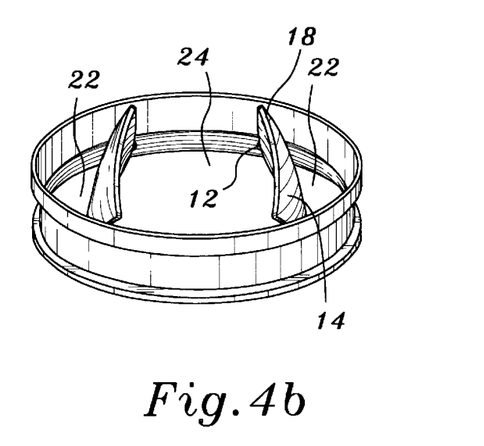
FIG. 4b shows the valve of FIG. 4a in an opened configuration.

FIGS. 2d, 2e and 2f show how the present invention ensures rapid closure while damping the slamming closure of many prior art valves. In cross-section the leaflets 14 present a curved appearance with the downstream 18 edges of the leaflets curving away from the support ring 20 and towards the center of the valve. This curvature may be cylindrical (i.e., the leaflets 14 form a portion of the surface of a cylinder) as shown in FIG. 3 so that the open valve presents straight edges 18 to the central opening 24, or the curvature may be spherical (i.e., the leaflets form a portion of the surface of a sphere) so that the open valve presents curved edges 18 to the central opening 24 as shown in FIG. 4. In either case, the curvature results in the downstream edges 18 of the leaflets 14 being displaced slightly closer to the centerline of the valve than the pivot 12. The curvature is apparent in FIG. 2a. Although this displacement will guarantee rapid valve closure, the design may also advantageously extend the curvature so that the upstream edges 18' are also located closer to the valve centerline than the pivots 12 when the valve is open as is shown in an alternative embodiment in FIGS. 5d and 5e.

When the blood flow changes to the back-flow direction (arrows 26'), the displacement of the edges 18, 18' causes the blood flow to exert more force on the downstream surface 32 near the downstream edge 18 than on the downstream surface 32 near the upstream edge 18' (FIG. 2d). This force causes the leaflets 14 to pivot towards the closed position (arrows 28') (FIG. 2e). Initially, the surface 32 of the upstream half of the leaflet 14 (near edge 18') is in the shadow of the downstream edge 18 so that the back flowing blood exerts virtually no force on it. As the downstream edges 18 pivot towards the center of the support ring 20 to close the central opening 24 (FIG. 2e), the surface 32 near the upstream edges 18' is moved into the lateral openings 22. As the upstream edges 18' close off the lateral openings 22, they interact with the back flowing blood, which imparts a force opposite to that imparted onto the surface 32 near the downstream edges 18.

Figure 6:
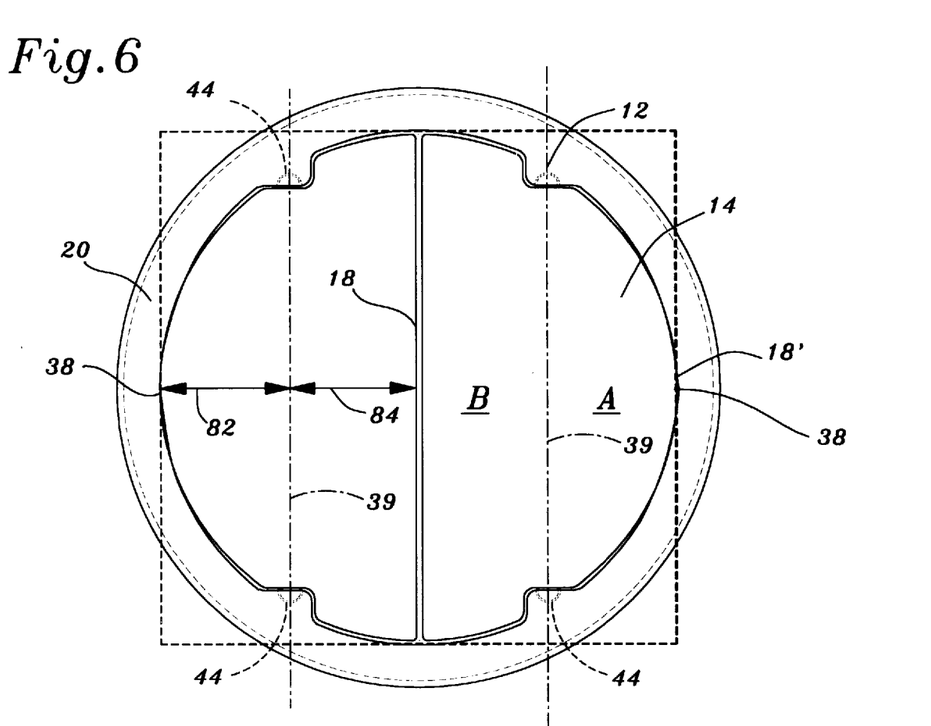
FIG. 6 show a surface view of a valve of the present invention with the leaflets in the closed position to demonstrate the surface area of each leaflet on either side of an imaginary line drawn from pivot to pivot.

The force opposing the closure of the upstream edges 18' is not sufficient to prevent closing of the valve. FIG. 6 demonstrates that the surface area of the leaflet 14 on the upstream side of the pivots 12 is smaller than the surface area on the downstream side. This is because a distance 82 from an upstream leaflet contact point 38 to an imaginary line 39 between the pivots 12 is equal to a distance 84 from the imaginary line 39 bisecting the distance (82+84) of the leaflet 14 to the downstream edge 18. With this arrangement it is plain that the area of the upstream portion of the leaflet is smaller because its area is significantly less than that of a rectangle A whose dimensions are the distance 82×the imaginary line 39, while the area of the downstream portion is only slightly less a rectangle B whose dimensions are the distance 84×the imaginary line 39 (wherein geometry indicates that rectangle A=rectangle B).

Therefore, the anticlosing force applied to the upstream leaflet area near the edge 18' is less than the closing force applied to the corresponding area near downstream edge 18. Thus, the opposing force merely causes the leaflet to decelerate before the closing impact as it approaches the fully closed position, thereby providing a damping effect to slow leaflet velocity at closure and thereby limit wear and tear on the valve, limit damage to red cells, and lessen the clicking sound that is typical of artificial heart valves. The damping effect is sufficient to reduce impact and the resulting closing sound below the hearing acuity of many patients. This damping effect will exist as long as the imaginary line 39 bisects or nearly bisects a radius of the leaflet 14. If the pivots 12 are moved towards the downstream edge 18, the area of rectangle A and the anticlosing force will increase. Although damping will increase, the overall closing speed will be reduced. At the same time, the central opening 24 will be reduced. Moving the pivots 12 towards the upstream reduces the damping effect. Therefore, the optimal placement of the pivots 12 is near, but not necessarily on, the imaginary line 39 that exactly bisects a radius of the leaflet 14.

Figures 5A, 5B, 5C:
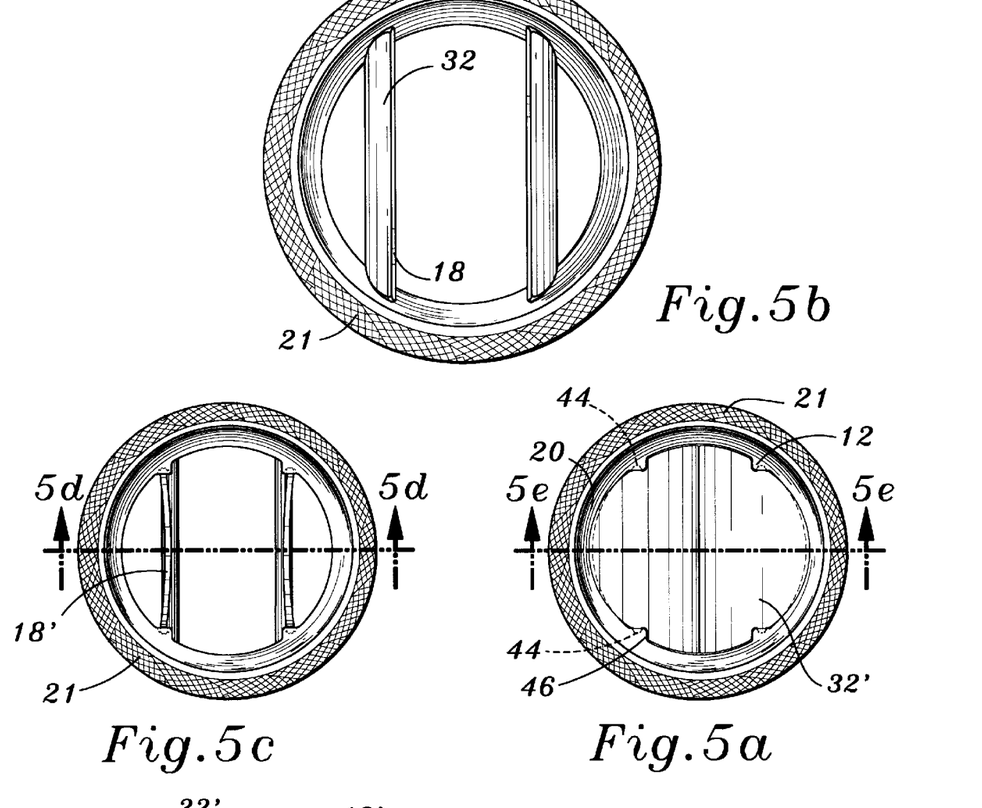
FIG. 5a shows a surface view of the bileaflet valve of FIG. 2 in the closed position from the upstream (inflow) side.
FIG. 5b shows a surface view of the bileaflet valve of FIG. 2 in the opened position from the downstream (outflow) side.
FIG. 5c shows a surface view of the bileaflet valve of FIG. 2 in the opened position from the upstream (inflow) side.
Figure 5D:
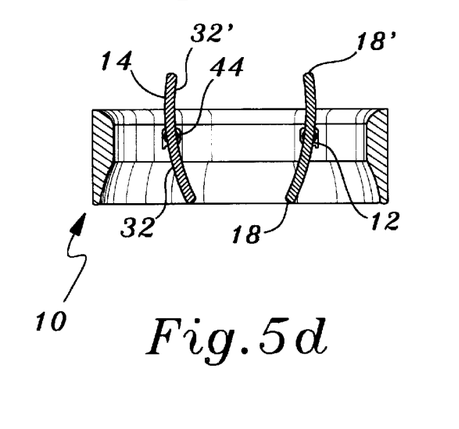
FIG. 5d shows a cross-section of an alternative embodiment, in the opened configuration, of the present invention wherein both the upstream and the downstream portions of the leaflets are curved.
Figure 5E:
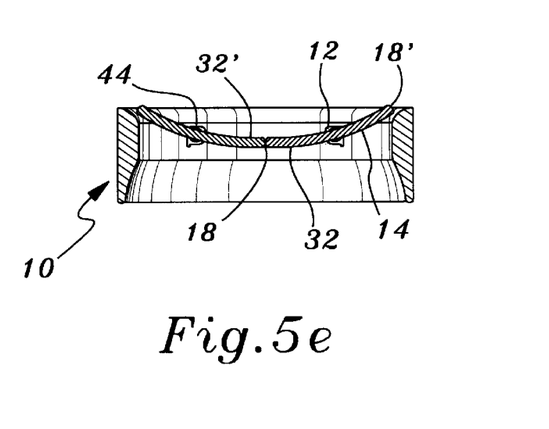
FIG. 5e shows the valve of FIG. 5d in the closed position.

Unlike the prior art valves where the back flowing blood causes a central turbulence, the back flowing blood is directed towards the lateral openings by the convex downstream curvature of the leaflets 14 and because the lateral opening 22 close last (arrows 36) (FIG. 2f). This causes the blood to make a laminar sweep over the smoothly curved leaflet surface, thereby removing any incipient clots and ensuring that fresh blood sweeps the periphery of the support ring 20 including the pivots 12. The soft closure provided by the damping effect also reduces damage to blood cells that might be trapped between the leaflets 14 and the support ring 20 when the leaflets pivot into the closed position. The leaflets 14 are designed to minimize crushing damage to blood cells. FIG. 5a shows a view of the closed valve from above. This drawing shows a suture ring 21 which surrounds the valve body 20 and is used by a surgeon in suturing the valve in place in a heart. Note that where the downstream edges 18 of the leaflets come together there is a small gap. This gap prevents blood cells from being crushed and damaged when the valve closes, and although the gap also permits a small amount of blood leakage through the closed valve, this volume of leakage is clinically insignificant and allows the blood to effectively wash all of the valve components. On the other hand, most of the prior art bileaflet valves such as those described above are designed so that the leaflets 14 seal against each other upon closing, thereby preventing surface washing and promoting blood cell damage.

A small gap also exists between the upstream edges 18' of the leaflets and the support ring 20 when the leaflets close the lateral openings 22. The leaflets 14 contact the support ring 20 at only the single contact point 38 for each leaflet. By contacting at the single point 38 instead of all around the periphery of the leaflet, the area in which blood cell damage can occur is greatly diminished. Moreover, contact at the point 38 during valve closing acts as a stop to ensure that the downstream edges 18 do not ever meet, but are held slightly apart. The contact point 38 can be created by producing a slight protuberance or extension of the leaflet so that that point meets the support ring 20 before the rest of the upstream edge 18' does, and/or there can be a slight protuberance on the support ring 20. In either of these situations the protuberance(s) prevent the upstream edges 18' from striking the support ring 20 and prevent the downstream edges 18 from striking each other.

The curvature of the laminar leaflets 14 ensures initial rapid closing of the valve upon reversal of blood flow. The laminar leaflets 14 are curved so that the leaflet surface 32 exposed on the downstream side of the closed valve is convex while the leaflet surface 32' on the upstream side of the closed valve is concave. The curved surfaces provided by the leaflet 14 are amenable to smooth, laminar flow over the leaflet surfaces during closing (arrows 36). When the valve is closed the leaflets 14 display a concave spherical or cylindrical surface to the upstream (inflow) side of the valve and a convex spherical or cylindrical surface to the downstream (outflow) side.

Figure 7A:
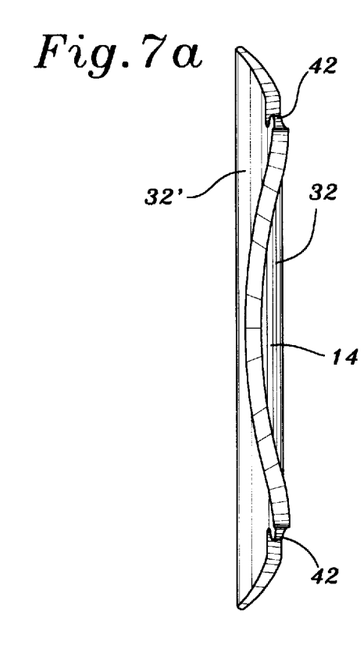
FIG. 7a shows one of the leaflets of the valve of FIG. 2 from the side in the opened position to illustrate an ear, part of the pivot structure, and the curvature of the leaflet.
Figure 7B:
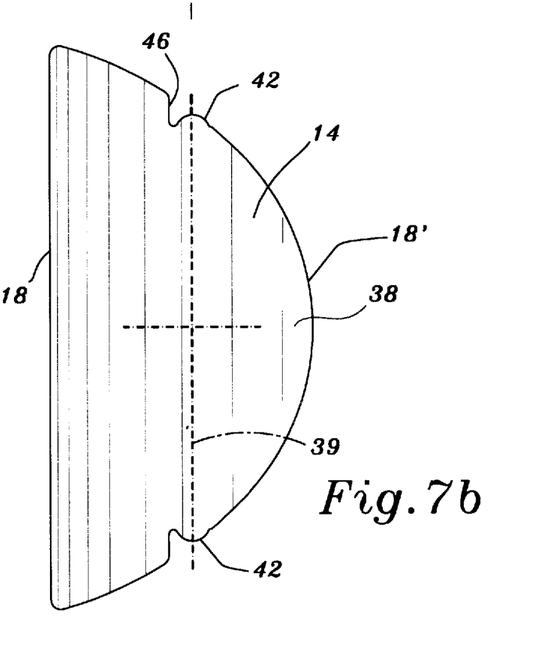
FIG. 7b shows a surface view of the leaflet of FIG. 7a to better illustrate the ear.
Figure 8:
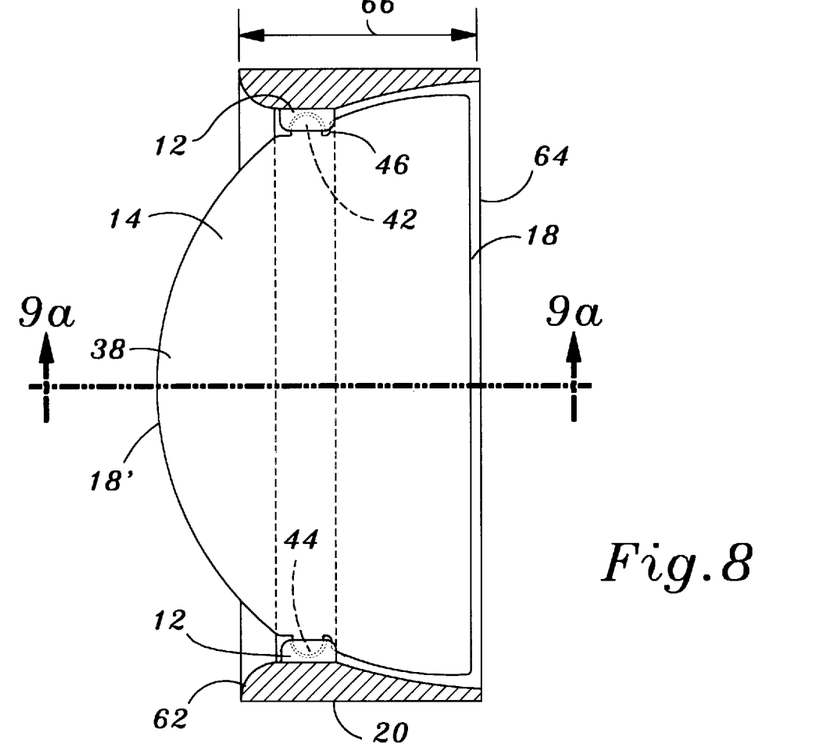
FIG. 8 shows a cross-section of the present invention to illustrate the interaction with the ear and a socket on the support ring.

FIG. 7b shows a surface view of one of the leaflets 14. On the leaflet 14 the pivots 12 are provided by two ears 42 which each mate with sockets 44 on the support ring 20 (FIG. 8). In a preferred embodiment the ears 42 are formed from the leaflet 14 having flat upper and lower surfaces continuous with, or slightly tapering form, the surfaces 32, 32' of the leaflet 14 (i.e., the ears are flat, see FIG. 7a). An actual contact surface between the ear 42 and the support ring 20 is rounded to minimize the actual wearing contact between the leaflet 14 and the support ring 20. Of course, other shapes to minimize contact area such as a point (triangular shaped ear) are possible. Wear can be further minimized by inserting a region of specially hardened material (i.e., ruby, sapphire, etc.) at the contact point between the ear 42 and the socket 44 on either the ear 42 or the socket 44 or both, rather like a watch jewel bearing. The leaflet 14 also has an ear cutout 46 in the vicinity of the ear. The cutout 46 provides clearance and interaction with the socket 44 as explained below. While the drawings show the ears 42 on the leaflets 14 and the sockets 44 on the support ring 20, it is a simple matter to reverse these positions and put the sockets 44 on the leaflets 14 and the ears 42 on the support ring 20.

FIG. 8 shows a cross-section through the support ring 20 in the open position. While the pivots 12 are symmetrically placed in reference to a distance from the contact point 38 to the downstream edge 18 of the leaflet 14, the pivots are not symmetrically placed in relation to a height 66 of the support ring 20. That is, the pivots 12 are closer to the upstream edge 62 than to the downstream edge 64 of the support ring 20. This slight asymmetry allows the support ring height 66 to be minimized by having the upstream edges 18' protrude slightly from the support ring 20 in the open position. The downstream leaflet edge 18 should remain protected within the support ring 20 because the structure of the heart is such that the downstream area of a valve is much more likely to encounter obstructions than the upstream portion, particularly when the valve is used in the mitral position. Thus, the present invention provides an essentially nonleaflet profile valve; that is, when the valve is open, the leaflets 14 are not exposed at all on the downstream side. Another important feature is that the entire downstream (at edge 64) exit (i.e., internal diameter) of the support ring 20 is larger than the upstream entrance (at edge 62). This makes the downstream exits from the lateral openings 22 larger than their respective upstream entrances. This promotes nonturbulent and overall flow across the valve. The curvature of the downstream edges 18 of the leaflets 14 also contributes to the increased downstream exit size of the lateral openings 22.

Figure 9A:
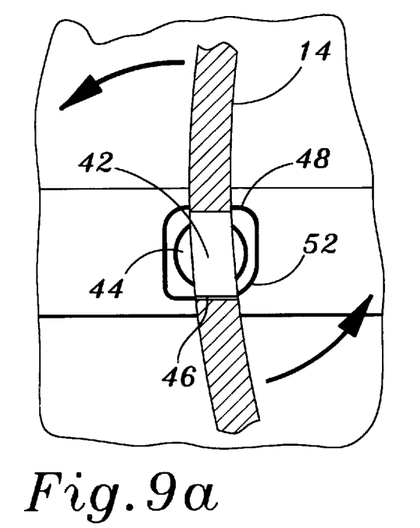
FIG. 9a shows a cross-section in a plane normal to the section of FIG. 8 with the leaflets in the opened position.
Figure 9B:
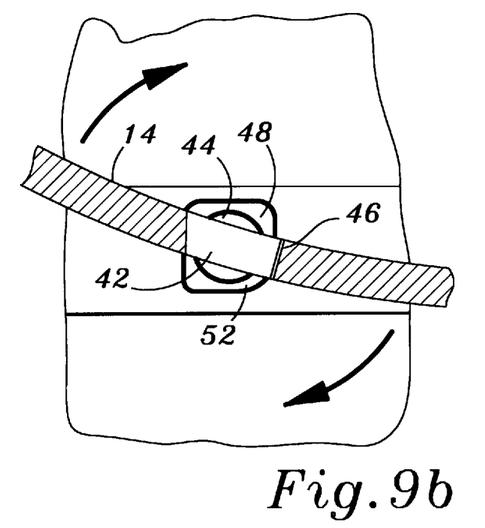
FIG. 9b shows a cross-section in a plane normal to the section of FIG. 8 with the leaflets in the closed position.
Figure 10A:
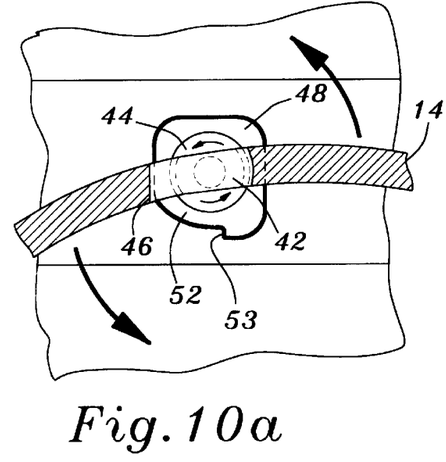
FIG. 10a shows a cross-section of an alternative embodiment valve in a plane normal to the section of FIG. 8 with the valve in the closed position.
Figure 10B:
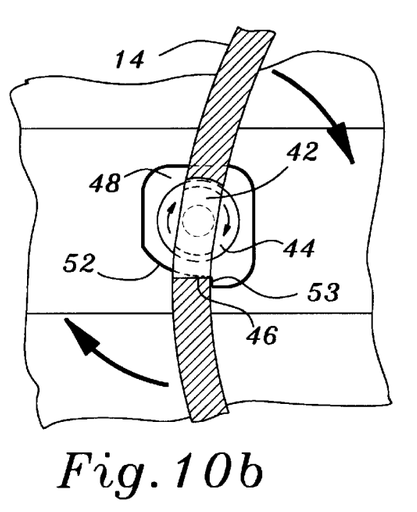
FIG. 10b shows a cross-section of an alternative stop design in a plane normal to the section of FIG. 8 with the valve in the opened position.

In FIG. 8 the ear 42 can be seen inserted into the socket 44, which is partially raised from an inner surface of the support ring 20. Note that the ear cutout 46 which provides clearance for the socket 44 when the leaflets 14 are in the closed position (see FIG. 6) actually contacts the socket 44 and acts as a stop in the full open position. This can be more readily seen in FIG. 9a (open) and FIG. 9b (closed), which show a cross-section taken normal to the plane of section of FIG. 8. Here the interaction between the ear cutout 46 and the socket 44 can be more readily appreciated in the open position.. An outer side wall 48 of the socket 44 is curved with a radius equivalent to a distance of the cutout 46 from the center or rotation (i.e., center of the ear 42) of the pivot 12. This radius increases, however, on a lower surface 52. When the leaflet 14 is in the closed position there is a clearance between the cutout 46 and the socket 44, but when the leaflet 14 pivots into the opened position (see FIG. 9a), the cutout 46 contacts the lower surface 52 and prevents further pivoting of the leaflet. This stop is provided so that the leaflets 14 do not over open or oscillate and so that the downstream area near the edges 18 is held in the optimal position for interacting with reverse blood flow to close the valve. Because the blood is flowing along both the downstream and upstream surfaces 32, 32' of each leaflet 14 as the leaflets approach the opened position, the opening velocity of the leaflets is greatly slowed so there is little impact or wear between the cutout 46 and the lower surface 52 of the socket 44. FIG. 10a and 10b show comparable view of an alternative stop design. Here the lower outer surface 52 of the socket 44 is provided with a pronounced step 53 which interacts with the ear cutout 46 to act as a stop in the open position (FIG. 10b).

Figure 11A:
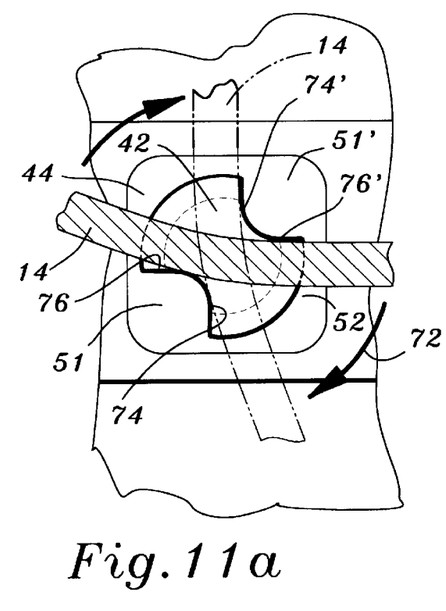
FIG. 11a shows the pivots of an alternative embodiment wherein two rounded stops within the socket control leaflet motion.
Figure 11B:
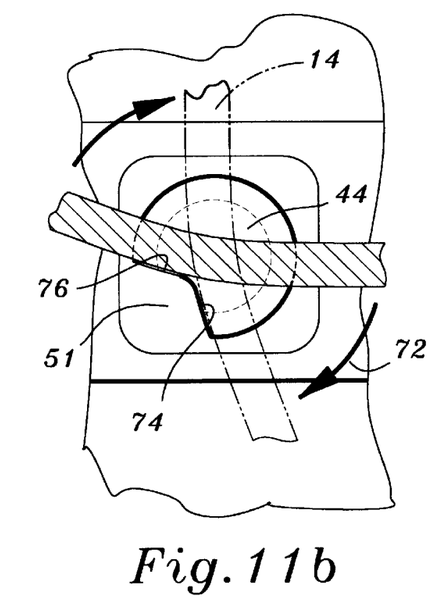
FIG. 11b shows the pivots of an alternative embodiment wherein one rounded stop within the socket controls leaflet motion.

Alternative embodiments shown in FIGS. 11a and 11b uses rounded stops 51 located within the socket to provide a stop (stops) so that the leaflets 14 do not over open and are, therefore, positioned in an optimal position for closing upon reversal of flow. The embodiment shown in FIG. 11a has two of the rounded stops 51, 51' constricting the open area of the socket 44 to an hour glass shape. When the leaflet 14 is in the opened position it contacts the flat or curved (configured to match the surface of the leaflet which may be either straight or curved) surfaces 74, and 74' of stops 51 and 51', respectively. In the closed position the leaflet interacts with surfaces 76, and 76' of stops 51 and 51', respectively. The stops in the closed position may be in lieu of the contact point 38 or as a backup stop to compensate for wear of the contact point 38. The embodiment shown in FIG. 11b has only one stop 51, but otherwise behaves similarly to the structure just described.

The choice of fabrication materials for heart prostheses is well known to one of ordinary skill in the art. Suffice it to say that like all mechanical devices prosthetic valves are subject to wear which may result in premature failure. Titanium and other immunologically acceptable metals (i.e., Stellite) have been employed especially for the support ring 20. Pyrolite and similar forms of mechanically hard amorphous (pyrolytic) carbon are currently materials of choice for fabrication of prosthetic heart valves, especially for the leaflets 14. Hard material intended to resist wear often result in noise when part strikes part. The discernible clicking sound is often extremely disturbing to patients. The present invention deals with the noise problem and limits leaflet wear by damping the leaflet movement during valve closure as explained above.

What is claimed is:

1. An improved bileaflet prosthetic heart valve comprising:
   a cylindrical support ring having a central orifice for blood to flow through when said valve is open;
   two leaflets for occluding the central orifice for preventing a reverse blood flow through the central orifice, each leaflet substantially semicircular in outline and pivotally suspended within the support ring by a pair of centrally disposed pivot means, wherein an imaginary line drawn between the pivot means of each leaflet substantially perpendicular to and substantially bisecting an axis of bilateral symmetry of each leaflet defines, on a first side of the line, an upstream leaflet portion whose semicircular edge approaches an inner wall of the support ring when the leaflets are in a closed position and, on a second side of the line, a downstream leaflet portion, edges of which downstream leaflet portion closely approach each other along a diameter of the central orifice when the leaflets are in the closed position, and with each leaflet curved in a cross-section taken perpendicular to said line between the pivot means so that a downstream end of each leaflet is disposed closer to said diameter of the central orifice than is said line between the pivot means when the leaflets are in an opened position;

a point of contact between each upstream leaflet portion and the support ring forming a sole point of contact therebetween when the leaflets are in the closed position, leaving clearance between the support ring and remaining upstream leaflet portions and preventing the downstream edges of the leaflets from touching each other;

complementary means disposed on the central orifice in juxtaposed relation with the pivot means of the leaflets for interacting with said pivot means to pivotally suspend the leaflets; and stop means for restricting pivoting of the leaflets wherein the leaflets cannot pivot beyond the opened position.

2. The improved bileaflet heart valve of claim 1, wherein the pivot means are provided by sockets and the complementary means are provided by rounded ears which fit into said sockets.

3. The improved bileaflet heart valve of claim 1, wherein the pivot means are provided by rounded ears and the complementary means are provided by sockets into which said ears fit.

4. The improved bileaflet heart valve of claim 3, wherein the stop means are provided by two wedge-shaped members projecting into each socket leaving an hour glass shaped open space for the ears to occupy.

5. The improved bileaflet heart valve of claim 1, wherein valve opening and closing velocity is damped by locating the pivot means closer to the downstream edges of each leaflet to increase a surface area of the upstream portion of each leaflet.

6. The improved bileaflet heart valve of claim 1, wherein valve opening and closing velocity is damped by locating the pivot means to increase a surface area of the upstream leaflet portion relative to the downstream leaflet portion of each leaflet.

7. The improved bileaflet heart valve of claim 3, wherein the stop means are provided by an interaction between an outer surface of the socket and a portion of a juxtaposed leaflet.

8. The improved bileaflet heart valve of claim 1, wherein the leaflets are curved in a cross-section taken perpendicular to said line between the pivot means so that both an upstream end of each leaflet and the downstream end of each leaflet are closer to said diameter of the central orifice than is said line between the pivot means when the leaflets are in the opened position.

9. The improved bileaflet heart valve of claim 1, wherein the pivot means and the complementary means are disposed in relation to a height of the support ring so that the downstream end of each leaflet does not protrude beyond a downstream edge of the support ring when the leaflets are in the opened position.

10. The improved bileaflet heart valve of claim 1, wherein curvature of the leaflets is spherical so that the downstream ends of the leaflets that closely approach each other, when the leaflets are in the closed position, are curved in a cross-section taken parallel to said line between the pivot means.

11. The improved bileaflet heart valve of claim 1, wherein curvature of the leaflets is cylindrical so that the downstream ends of the leaflets that closely approach each other, when the leaflets are in the closed position, are straight in a cross-section taken parallel to said line between the pivot means.

12. An improved bileaflet prosthetic heart valve comprising:

a support ring having a central orifice for blood to flow through when the valve is open;

two leaflets for occluding the central orifice for preventing a reverse blood flow through the central orifice, each leaflet substantially semicircular in outline and pivotally suspended within the support ring by a pair of centrally disposed pivot means, wherein an imaginary line drawn between the pivot means of each leaflet is substantially perpendicular to and substantially bisects an axis of bilateral symmetry of each leaflet, thereby defining, on a first side of the line, an upstream leaflet portion whose semicircular edge approaches an inner wall of the support ring when the leaflets are in a closed position and, on a second side of the line, a downstream leaflet portion, ends of which downstream leaflet portion closely approach each other along a diameter of the support ring when the leaflets are in the closed position, and with each leaflet curved in a cross-section taken perpendicular to said line drawn between the pivot means;

complementary means disposed on the support ring in juxtaposed relation with the pivot means of the leaflets for interacting with said pivot means to pivotally suspend the leaflets; and stop means for restricting pivoting of the leaflets wherein the leaflets cannot pivot beyond the opened position and wherein the downstream ends of the leaflets do not touch in the closed position.

13. The improved bileaflet heart valve of claim 12, wherein the pivot means are provided by sockets and the complementary means are provided by rounded ears fitting into the sockets.

14. The improved bileaflet heart valve of claim 12, wherein the pivot means are provided by rounded ears and the complementary means are provided by sockets into which the rounded ears fit.

15. The improved bileaflet heart valve of claim 14, wherein the stop means are provided by two wedge-shaped members projecting into each socket leaving an hour glass shaped open space occupied by the ears.

16. The improved bileaflet heart valve of claim 14, wherein the stop means are provided by a member projecting into each socket and by an interaction between an outer surface of the socket and a portion of a juxtaposed leaflet.

17. The improved bileaflet heart valve of claim 12, wherein valve opening and closing velocity is damped by locating the pivot means to increase a surface area of the upstream portion relative to the downstream portion of each leaflet.

18. The improved bileaflet heat valve of claim 12, wherein the leaflets are curved in a cross-section taken perpendicular to said line between the pivot means so that both an upstream end of each leaflet and the downstream end of each leaflet are closer to said diameter of the support ring than is said line between the pivots when the leaflets are in the opened position.

19. The improved bileaflet heart valve of claim 12, wherein curvature of the leaflets is spherical so that the downstream ends of the leaflets that closely approach each other, when the leaflets are in the closed position, are curved in a cross-section taken parallel to said line between the pivot means.

20. The improved bileaflet heart valve of claim 12, wherein curvature of the leaflets is cylindrical so that the downstream ends of the leaflets are straight in a cross-section taken parallel to said line between the pivot means.

21. The improved bileaflet heart valve of claim 12, wherein the complementary means and the pivot means are disposed in relation to a height of the support ring so that the downstream portion of the leaflets do not protrude beyond a downstream end of the supporting when the leaflets are in the opened position.

22. The improved bileaflet heart valve of claim 12, wherein the stop means for preventing the downstream leaflet edges from touching in the closed position are provided by a single point of contact between each leaflet and the support ring.

23. The improved bileaflet heart valve of claim 1, wherein the support ring is formed so that an inflow area on an upstream side of the orifice is smaller than an outflow area on a downstream side of the orifice.

24. The improved bileaflet heart valve of claim 12, wherein curvature of the leaflets suspended within the support ring is such that an inflow area of the lateral openings on an upstream side of the orifice is smaller than an outflow area of the lateral openings on a downstream side of The orifice.

25. The improved bileaflet heart valve of claim 12, wherein the upstream portion of each leaflet is straight in cross-section and the downstream portion of each leaflet is curved in cross-section, each cross-section taken perpendicular to said line between the pivot means, so that the downstream edge of each leaflet is closer to said diameter of the support ring than is said line between the pivots when the leaflets are in the opened position.

26. An improved bileaflet prosthetic heart valve comprising:
   a support ring having a central orifice for blood to flow through when the valve is open and
   two leaflets for occluding the central orifice for preventing a reverse blood flow through the central orifice, each leaflet pivotally suspended within the support ring by a pair of centrally disposed pivot means, wherein an imaginary line drawn between the pivot means of each leaflet is substantially perpendicular to and substantially bisects an axis of bilateral symmetry of each leaflet, thereby defining, on a first side of the line, an upstream portion of the leaflet whose semicircular edge approaches an inner wall of the support ring when the leaflets are in a closed position and, on a second side of the line, a downstream portion of the leaflet, an end of which downstream portion of a first leaflet closely approaches a respective downstream end of a second leaflet along a diameter of the support ring when the leaflets are in the closed position, and with each leaflet curved in a cross-section taken perpendicular to said line between the pivot means and the pivot means disposed so that an area of a central opening formed between the leaflets when the valve is in the opened position is twice as large as a combined area of two lateral openings also formed when the valve is in the opened position.

27. An improved bileaflet heart valve of a type wherein two pivoting leaflets are suspended in a central orifice to prevent reverse blood flow by pivoting into a closed position, the improvement comprising centrically pivoted curved leaflets, the leaflets being curved in a cross-section taken perpendicular to a line drawn between pivot means suspending the leaflets so that downstream leaflet ends are closer to a center of the orifice than are pivot means suspending the leaflets when the valve is in an opened position.

28. The improved bileaflet heart valve of claim 27, wherein load, wear and operative noise are reduced by disposing a pivot axis of a leaflet along a symmetric central axis of the leaflet.

* * * * *

UNITED STATES PATENT AND TRADEMARK OFFICE
CERTIFICATE OF CORRECTION

PATENT NO. : 5,814,099
DATED : September 29, 1998
INVENTOR(S) : Demetrio Bicer

It is certified that error appears in the above-identified patent and that said Letters Patent is hereby corrected as shown below:

Insert into Col. 6, line 11 as follows:

--From the upstream side in the opened--.

Col. 11, line 41, delete Claim 5 in its entirety and insert the following:

5. The improved bileaflet heart valve of Claim 3, wherein the stop means are provided by a member projecting into each socket.

Col. 13, line 34, delete "The" and insert --the--.

Signed and Sealed this

Seventeenth Day of August, 1999

Attest:

Q. TODD DICKINSON

Attesting Officer

Acting Commissioner of Patents and Trademarks